US00PP10098P

United States Patent [19]

Stravers

[11] Patent Number: Plant 10,098

[45] Date of Patent: Nov. 4, 1997

[54] GERBERA PLANT NAMED 'TERSNEL'

[75] Inventor: Lambertus Johannes Maria Stravers, Kudelstaart, Netherlands

[73] Assignee: Terra Nigra Holding B.V., De Kwakel, Netherlands

[21] Appl. No.: 574,102

[22] Filed: Nov. 28, 1995

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 7,253 6/1990 Segers ..... Plt./68.1

P.P. 8,589 2/1994 Stravers ..... Plt./68.1

*Primary Examiner*—Howard J. Locker

[57] ABSTRACT

A new and distinct cultivar of Gerbera plant named 'Tersnel', as illustrated and described, characterized by its single type, the pink ray florets which have solid pink color throughout, a green disc before flowering of the disc florets, darker pink male and female mature disc florets, the outermost florets which display soft pink stigmas and the middle florets showing yellow anthers, pink perianth lobe color and 110 mm overall flower diameter.

1 Drawing Sheet

BACKGROUND OF THE INVENTION

The present invention comprises a new and distinct cultivar of *Gerbera jamesonii*, referred to by the cultivar name 'Tersnel'. 'Tersnel' was originated from a hybridization program in De Kwakel, The Netherlands in 1990. The female parent was 'Terreino' and the male parent was unnamed seedling 88.107. The female parent 'Terreino' was pink, semi-double and had a black disc. The male parent 88.107 was lilac, single and had a green disc. The unnamed seedling 88.107 had no anthocyanin coloration at the base of the petiole nor the peduncle. This in contrast to the new cultivar 'Tersnel'. The female parent has been available outside Terra Nigra and is the subject of U.S. Plant Pat. No. 8,587. The male parent has not been available outside Terra Nigra and is not patented in the United States. The new cultivar was selected by me from the progeny of the stated parentage on or about February 1991. The first asexual reproduction of 'Tersnel' was accomplished when vegetative cuttings were taken on November 1991 in De Kwakel. The new cultivar is presently being propagated by cuttings and tissue culture. Horticultural examination of selected units initiated Mar. 1993 has demonstrated that the combination of characteristics as herein disclosed for 'Tersnel' are firmly fixed and are retained through successive generations of asexual reproduction.

'Tersnel' has not been observed under all possible environmental conditions. The phenotype may vary significantly with variations in environment such as temperature, light intensity and day length. The following observations, measurements and comparisons describe plants grown in De Kwakel, The Netherlands, under greenhouse conditions which closely approximate those generally used in commercial practice.

The following traits have been repeatedly observed and are determined to be basic characteristics of 'Tersnel', which in combination distinguish this Gerbera from its parents and all other varieties of which I am aware:

1. Type: Single.
2. Color of ray floret: Pink.
3. Color of disc before flowering disc florets: Green.
4. Color of perianth lobe: Pink.

5. Diameter of flower head: 100–110 mm.

Of the many commercial cultivars known to me, there is no cultivar similar in comparison to 'Tersnel'.

BRIEF DESCRIPTION OF THE FIGURE OF THE DRAWING

The accompanying photographic drawing shows typical inflorescence characteristics with the color being as nearly true as possible in illustrations of this type. In the following description, color references are made to The Royal Horticultural Society Color Chart (R.H.S.). The color values were determined at 15:00 p.m. on 15 Oct. 1992 under natural light at De Kwakel.

BOTANICAL DESCRIPTION OF THE PLANT

Botanical: *Gerbera jamesonii* cv. Tersnel.

Inflorescence

A. Capitulum:
- *Form.*—Incurving funnel-shaped.
- *Type.*—Single.
- *Diameter across face.*—100–110 mm.

B. Corolla of ray florets:
- *Color (general tonality from a distance of 3 meters).*—Pink.
- *Color (topside).*—R.H.S. 49A.
- *Color (bottom side).*—R.H.S. 27D.

C. Corolla of disc florets:
- *Color (mature).*—Pink.
- *Color (immature).*—Green/yellow.

D. Reproductive organs:
- *Stigma.*—Soft pink.
- *Anthers.*—Yellow.
- *Pappus.*—White.

Plant

A. General appearance:
- *Height.*—40 cm excluding any flowers.

B. Foliage:
- *Color (abaxial).*—R.H.S. 138B.
- *Color (adaxial).*—R.H.S. 137A.

*Shape.*—The angle of apex: acute. The shape of apex: pointed. The margin of lobes: serrate.

C. Disease resistance: No special disease resistance.

Other Characteristics

The following traits have been repeatedly observed and are determined to be basic characteristics of 'Tersnel', which in combination distinguish this Gerbera as a new and distinct cultivar.

Leaf blade:

*Length.*—Medium (approx. 40 cm).

*Width.*—Medium (approx. 18 cm).

*Thickness.*—Medium.

*Blistering.*—Medium.

*Pubescence.*—On upper side (midrib excluded): medium.

*Depth of cuts or incisions in leaf.*—Basal part: deep. Central part: deep. Distal part: weak.

*Color.—Upper side of the leaf blade: medium green (R.H.S.* 138B). Bottom side of the leaf blade: R.H.S. 137A.

*Glossiness on upper side.*—Medium.

*Angle of apex.*—Acute.

*Shape of apex.*—Pointed.

*Margin of lobes.*—Serrate.

*Extensions of margin.*—Medium.

*Petiole length.*—Medium (approx. 13 cm).

*Petiole coloration.*—Medium green R.H.S. 145B.

*Petiole anthocyanin coloration.*—Strong R.H.S. 183C at the base.

Peduncle:

*Length.*—Short to medium (50–55 cm).

*Cross section.*—Round.

*Tendency to fasciation.*—Absent.

*Thickness.*—Medium.

*Strength.*—Medium.

*Pubescence.*—Medium.

*Color.*—Medium green R.H.S. 144B.

*Anthocyanin coloration.*—At base: weak. At top: absent.

*Involucral bracts.*—Absent.

Flower head:

*Type.*—Single.

*Diameter.*—Medium (approx. 100–110 mm).

*Shape.*—Incurving funnel-shaped.

*Involucre.*—Height from point of attachment of involucre to top of flower head: medium (approx. 50 mm). Height: medium (approx. 22 mm). Diameter: medium (approx. 36 mm). Number of bracts: medium (approx. 40). Longitudinal axis of inner rows: reflexing. Anthocyanin: absent. Pubescence: medium.

*Ray florets.*—Number: medium (50). Shape: narrow elliptic. Longitudinal axis outer row: incurving. Longitudinal axis inner row: incurving.

*Outer ray floret.*—Cross section: convex. Length: medium (approx. 45 mm). Width: medium (approx. 11 mm). Longitudinal folding: medium. Angle of apex: acute. Shape of apex: pointed. Incisions of apex: one. Depth of incision: deep. Length of free petals: short. Color distribution on inner side: uniform. Edge of different color: absent. Striation: absent. Claw spot: present.

Disc florets:

*Diameter.*—Medium (approx. 25 mm).

*Main color perianth lobes.*—Female flowers: pink R.H.S. 68C. Male flowers: pink R.H.S. 68C.

Reproductive parts:

*Style.*—Main color distal part: light yellow.

*Stigma.*—Main color: soft pink.

*Anthers.*—Main color: yellow. Color of top relative to other parts is identical. Longitudinal stripes are absent. Intensity of anthocyanin coloration is absent or very weak.

*Pappus.*—Main color: white. Color of top relative to other parts is identical. Level of top relative to closed disc florets: same level.

*Fertility.*—Fertility as well as the seed setting is good.

I claim:

1. A new and distinct cultivar of Gerbera plant named 'Tersnel', substantially as herein shown and described, characterized particularly as to novelty by its characteristics enumerated above.

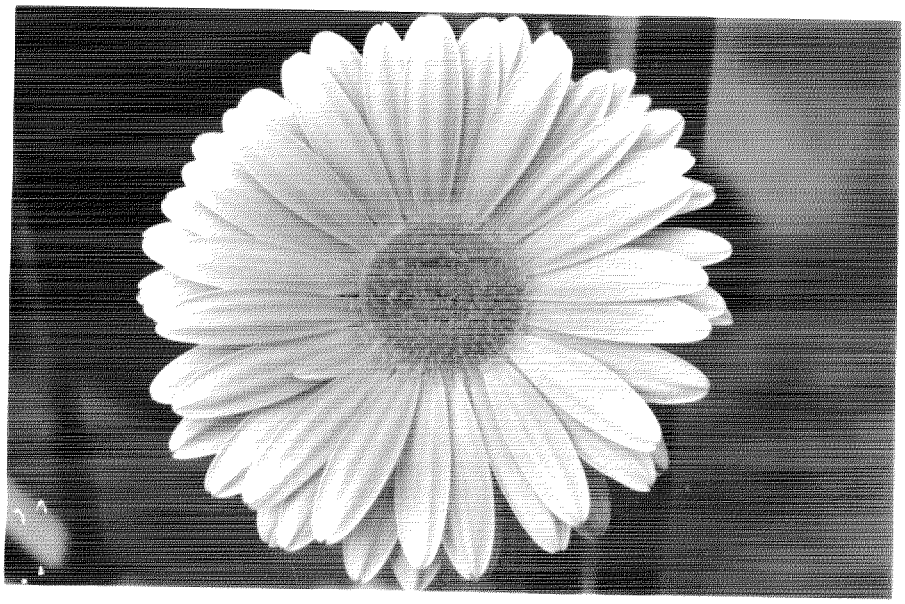

* * * * *